(12) United States Patent
Yip et al.

(10) Patent No.: US 12,129,886 B2
(45) Date of Patent: Oct. 29, 2024

(54) ORTHOPEDIC HINGE ASSEMBLY

(71) Applicant: THE HONG KONG POLYTECHNIC UNIVERSITY, Hong Kong (CN)

(72) Inventors: Yiu Wan Yip, Hong Kong (CN); Lai Hing Fok, Hong Kong (CN)

(73) Assignee: THE HONG KONG POLYTECHNIC UNIVERSITY, Hong Kong (CN)

( * ) Notice: Subject to any disclaimer, the term of this patent is extended or adjusted under 35 U.S.C. 154(b) by 1016 days.

(21) Appl. No.: 16/523,474

(22) Filed: Jul. 26, 2019

(65) Prior Publication Data
US 2020/0032839 A1    Jan. 30, 2020

(30) Foreign Application Priority Data
Jul. 27, 2018    (CN) .......................... 201821207195.7

(51) Int. Cl.
*F16C 11/04* (2006.01)
*A61F 5/02* (2006.01)

(52) U.S. Cl.
CPC ................ *F16C 11/04* (2013.01); *A61F 5/02* (2013.01); *A61F 5/026* (2013.01)

(58) Field of Classification Search
CPC ........ A61F 5/02; A61F 5/026; A41D 13/0531
See application file for complete search history.

(56) References Cited

U.S. PATENT DOCUMENTS

| | | | | |
|---|---|---|---|---|
| 1,316,915 A | * | 9/1919 | Meyer | A61F 5/028 602/19 |
| 5,685,831 A | * | 11/1997 | Floyd | A61F 5/026 602/17 |
| 6,063,047 A | * | 5/2000 | Minne | A61F 5/02 602/5 |
| 2008/0021357 A1 | * | 1/2008 | Firsov | A61F 5/026 602/19 |
| 2010/0263111 A1 | * | 10/2010 | Leatt | A41D 13/0531 2/467 |
| 2014/0224849 A1 | * | 8/2014 | Hiemenz | A41D 13/0531 224/271 |
| 2017/0196722 A1 | * | 7/2017 | Murdock | A61F 5/028 |
| 2021/0106449 A1 | * | 4/2021 | Norton | B33Y 80/00 |

* cited by examiner

*Primary Examiner* — Ophelia A Hawthorne
*Assistant Examiner* — Gina McCarthy
(74) *Attorney, Agent, or Firm* — Yue (Robert) Xu; Apex Attorneys at Law, LLP

(57) ABSTRACT

An orthopedic hinge assembly is provided, which includes a V-shaped blade, an intermediate blade and a terminal blade. The V-shaped blade, the intermediate blade and the terminal blade are provided with holes to allow a fixed member to pass through; the V-shaped blade is hinged to one end of the intermediate blade for supporting the bending of a body; another end of the intermediate blade is hinged to the terminal blade for supporting the bending of the body; the strip-shaped grooves on the V-shaped blade, the intermediate blade and the terminal blade can be used to fix the orthopedic hinge assembly to a surface of the body using a belt or other fixed member, and to make the corrective member stably fix to one side of the body, effectively producing the lateral corrective force; the design of each blade can coordinate the forward bending motion of the body, effectively introducing the corrective force.

8 Claims, 6 Drawing Sheets

ORTHOPEDIC HINGE ASSEMBLY

CROSS REFERENCE TO RELATED APPLICATIONS

This application claims the priority to Chinese patent application No. 201821207195.7, titled "ORTHOPEDIC HINGE ASSEMBLY", filed with the China National Intellectual Property Administration on Jul. 27, 2019, the entire disclosure of which is hereby incorporated by reference.

FIELD

The present application relates to rehabilitation orthotic devices, and in particular to an orthopedic hinge assembly.

BACKGROUND

An orthosis is an external medical device for a body to support different body parts, correct body deformities, protect body parts or assist in body movement and further to improve body function. A three-point pressure system is a basic corrective principle of using the orthosis. The system includes a main force acting in one direction and two reaction forces acting in opposite directions, which are located at proximal and distal ends of the main force. In this case, an asymmetric design is usually used to maximize the effectiveness of the corrective force. Therefore, the three-point pressure system is commonly used for the asymmetrical device such as a scoliosis orthosis, a knee and ankle orthosis, and even a finger splint.

One of the most commonly used materials in the orthosis is rigid thermoplastic due to the strength and castability, however, limited flexibility, manufacturing difficulties, and inadequate equipment stability are the usual disadvantages of the thermoplastic orthosis, especially for members that are required to cover a joint. Since the device is unable to match a normal motion of the joint, the rotation of the device and the gap between the device and the skin may result in skin abrasion and abnormal stresses on the joint.

Therefore, there currently are many different types of orthopedic assemblies and orthopedic hinge assemblies that are used in the orthosis to improve the mobility limitations. In the conventional technology, some orthopedic hinge assemblies are positioned even along the sagittal plane of the joint, thereby allowing for moderate forward bending and stabilization of the device. However, when such an orthopedic hinge assembly is used along the sagittal plane of the joint, it is difficult to apply lateral corrective force, and at the same time, it is difficult to leave sufficient space on the other side of the body to align the body, and it is difficult to adapt to the size of different parts of the body.

SUMMARY

To solve the above technology problem, a main object of the present application is to provide an orthopedic hinge assembly.

The following technology solutions are provided according to the present application.

An orthopedic hinge assembly includes a V-shaped blade or/and an intermediate blade or/and a terminal blade. The V-shaped blade or/and the intermediate blade or/and the terminal blade are provided with holes to allow a fixed member to pass through; the V-shaped blade is hinged to one end of the intermediate blade for supporting the bending of a body; or/and another end of the intermediate blade is hinged to the terminal blade for supporting the bending of the body; or/and the V-shaped blade is hinged to the terminal blade for supporting the bending of the body.

Preferably, the holes provided on the V-shaped blade, the intermediate blade, and the terminal blade are: grooves, circular holes, triangular holes, and square holes.

Preferably, the holes provided on the V-shaped blade, the intermediate blade, and the terminal blade are: 1 to 10 strip-shaped grooves of the V-shaped blade that are provided on both sides of the V-shaped blade; 1 to 20 strip-shaped grooves of the intermediate blade that are provided on both sides of the intermediate blade; 1 to 20 strip-shaped grooves of the terminal blade that are provided on both sides of the terminal blade.

Preferably, 1 to 20 strip-shaped grooves of the intermediate blade are provided in the middle of the intermediate blade; and 1 to 20 strip-shaped grooves of the terminal blade are provided in the middle of the terminal blade.

Preferably, no intermediate blade may be provided, or, one intermediate blade may be provided, or, 2 to 20 intermediate blades may be provided.

Preferably, one end of the V-shaped blade is a furcated end of the V-shaped blade; both ends of the intermediate blade are furcated ends of the intermediate blade; one end of the terminal blade is a furcated end of the terminal blade; the furcated end of the V-shaped blade is hinged to the furcated end of the intermediate blade at one end of the intermediate blade by a first pin of the orthopedic hinge assembly pin; and the furcated end of the intermediate blade at another end of the intermediate blade is hinged to the furcated end of the terminal blade by a second pin of the orthopedic hinge assembly.

Preferably, any two of the furcated end of the V-shaped blade, the furcated ends of the intermediate blade, and the furcated end of the terminal blade form a structure having at least one convex portion and at least one concave portion are fitted to each other.

Preferably, shapes of the V-shaped blade, the intermediate blade, and the terminal blade are adapted to a using part of the body.

Preferably, the V-shaped blade, the intermediate blade, and the terminal blade have a plate shape.

A garment with a corrective function is further provided according to the present application, which includes any one of the above orthopedic hinge assembly.

The orthopedic hinge assembly is provided according to the present application, which includes the V-shaped blade, the intermediate blade and the terminal blade. The V-shaped blade, the intermediate blade and the terminal blade are provided with holes to allow a fixed member pass through; the V-shaped blade is hinged to one end of the intermediate blade for supporting the bending of a body; another end of the intermediate blade is hinged to the terminal blade for supporting the bending of the body; the strip-shaped grooves on the V-shaped blade, the intermediate blade, and the terminal blade can be used to fix the orthopedic hinge assembly to the plane of the body using a belt or other fixed member, and to make the corrective member stably fix to one side of the body for stabilizing the orthosis, thereby allowing the lateral corrective force to be effectively caused; the orthopedic hinge assembly design of each blade can coordinate the forward bending motion of the body, thereby effectively introducing the corrective force, which is also consistent with the body movement; and the material of each member can be rigid and can prevent the rotation of the orthosis and the loss of the corrective force.

BRIEF DESCRIPTION OF THE DRAWINGS

For clearer illustration of the technical solutions according to embodiments of the present application or conventional technology, hereinafter are briefly described the drawings to be applied in embodiments of the present application or conventional techniques. Apparently, the drawings in the following descriptions are only some embodiments of the present application, and other drawings may be obtained by those skilled in the art based on the provided drawings without creative efforts.

Figure 1:
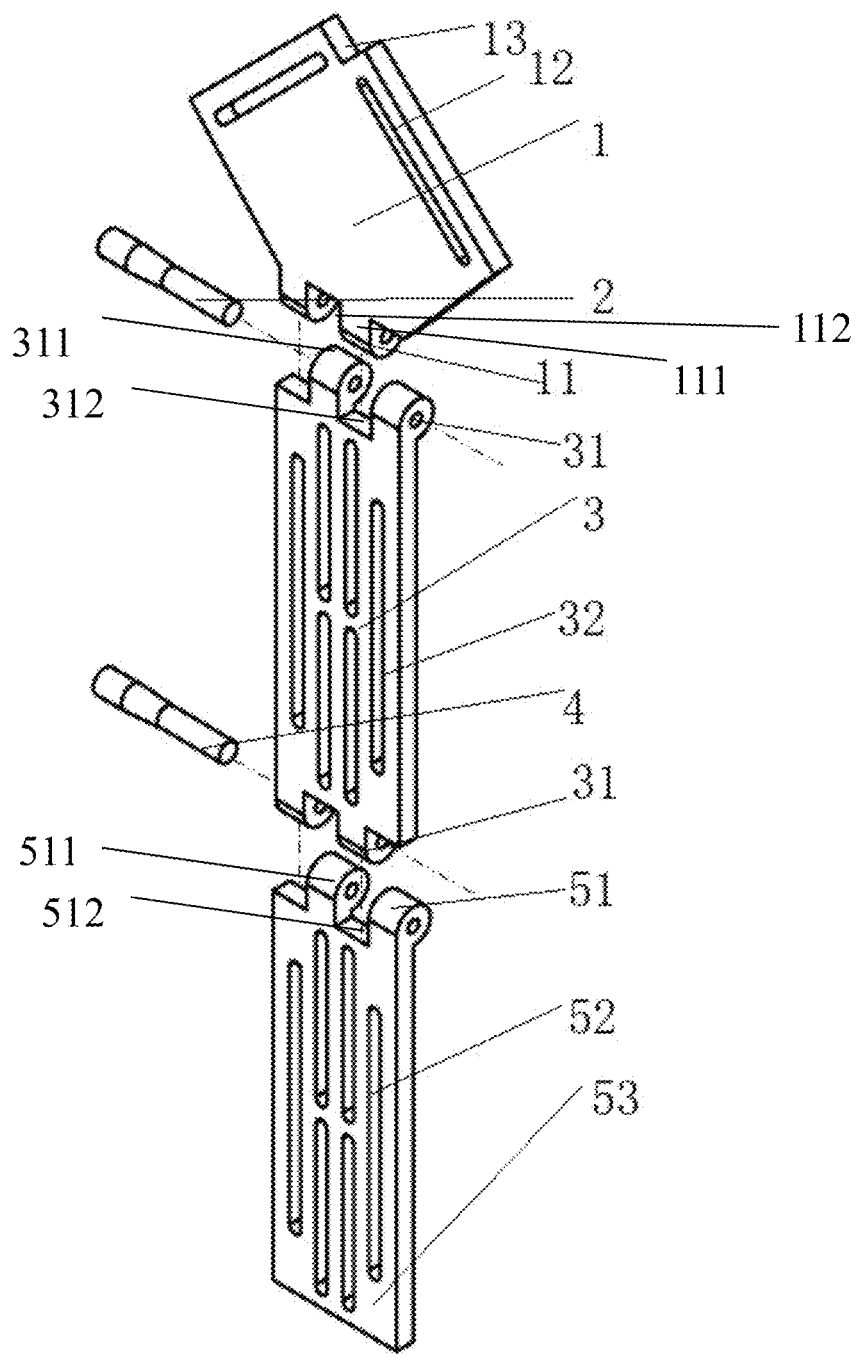
FIG. 1 is an exploded view of an orthopedic hinge assembly according to the present application.
Figure 2:
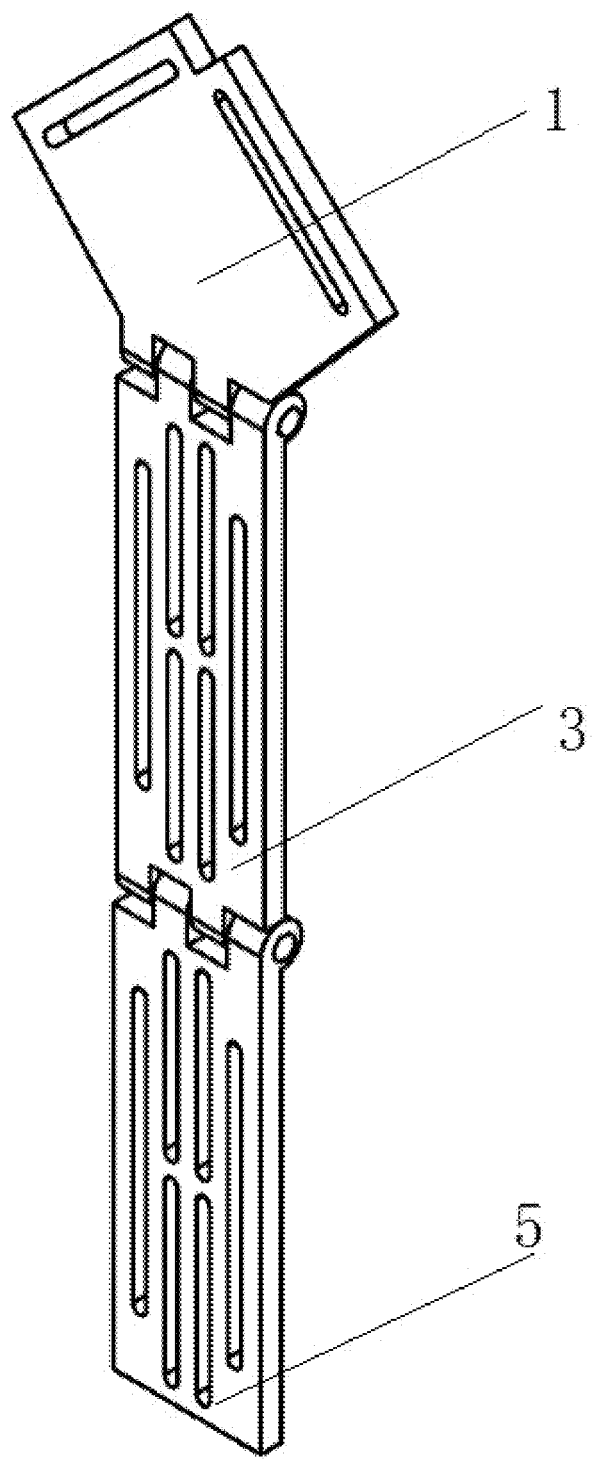
FIG. 2 is an isometric view of the orthopedic hinge assembly according to the present application.
Figure 3:
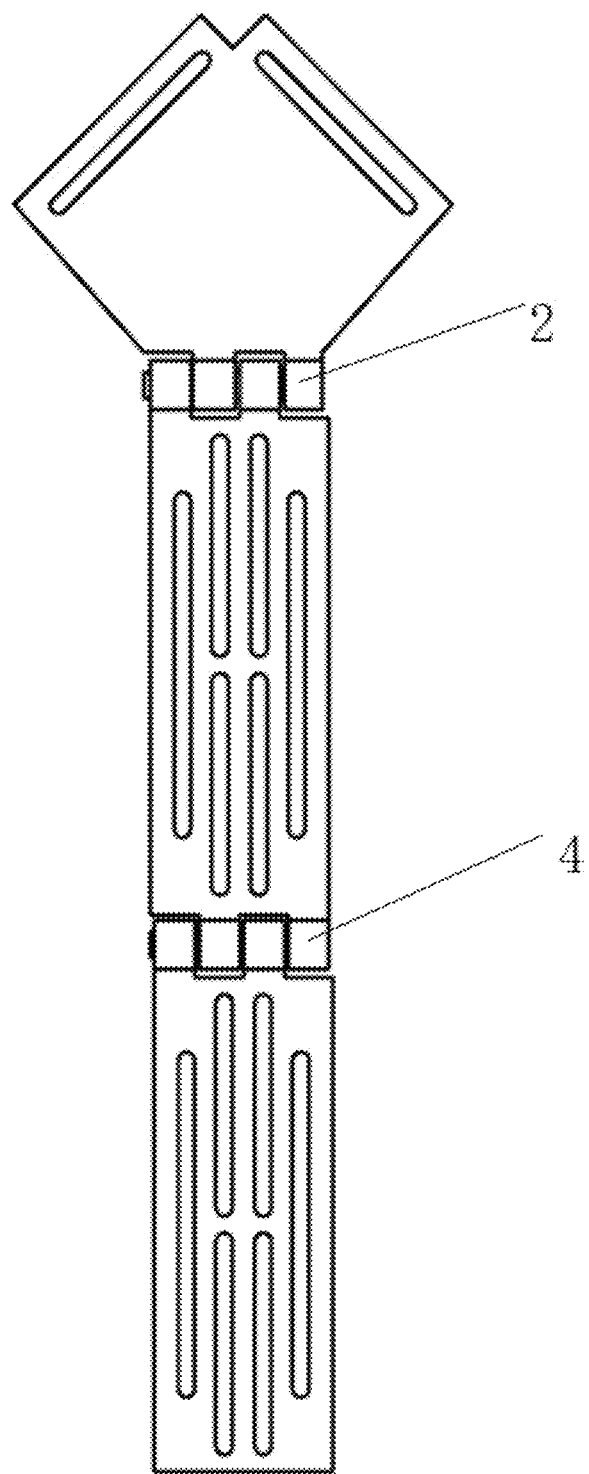
FIG. 3 is a front view of the orthopedic hinge assembly according to the present application.
Figure 4:
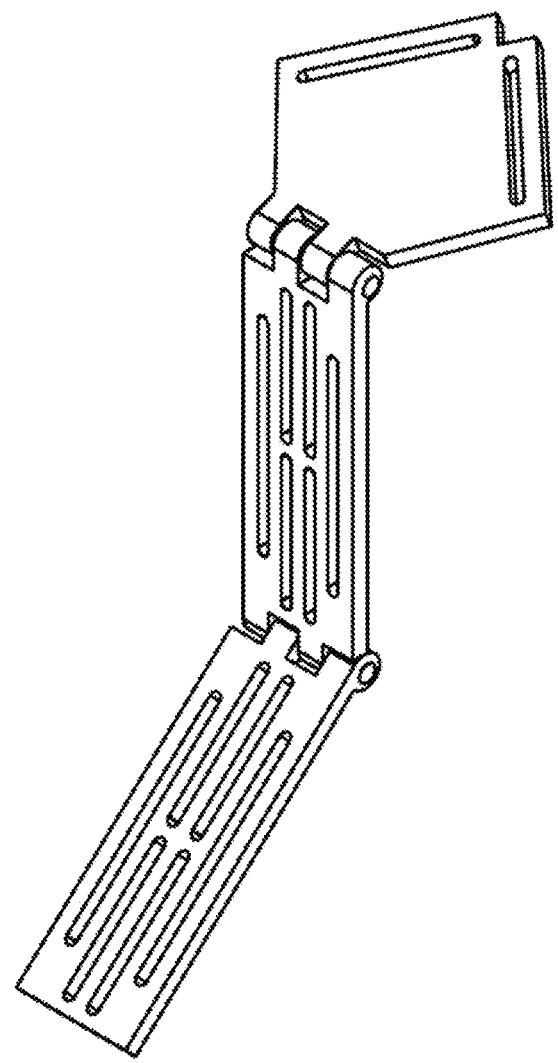
FIG. 4 is a schematic view of the orthopedic hinge assembly in a bent state according to the present application.

| Reference Numerals: | |
|---|---|
| 1 V-shaped blade, | 11 furcated end of V-shaped blade, |
| 12 strip-shaped groove of V-shaped blade, | 13 open end of V-shaped blade, |
| 2 first hinge pin, | 3 intermediate blade, |
| 31 furcated end of intermediate blade, | 32 strip-shaped groove of intermediate blade, |
| 4 second hinge pin, | 5 terminal blade, |
| 51 furcated end of terminal blade, | 52 strip-shaped groove of terminal blade, |
| 53 flat end of terminal blade, | |
| 111 convex portion of furcated end of V-shaped blade, | |
| 112 concave portion of furcated end of V-shaped blade, | |
| 311 convex portion of furcated end of intermediate blade, | |
| 312 concave portion of furcated end of intermediate blade, | |
| 511 convex portion of furcated end of terminal blade, | |
| 512 concave portion of furcated end of terminal blade, | |
| 6 fixing member of the scoliosis orthosis, | 7 shoulder belt, |
| 8 corrective member. | |

DETAILED DESCRIPTION

The technical solutions according to embodiments of the present application are described clearly and completely hereinafter in conjunction with the drawings in the embodiments of the present application. Apparently, the described embodiments are only a part of the embodiments of the present application, rather than all embodiments. Based on the embodiments in the present application, all of other embodiments, made by the person skilled in the art without any creative efforts, fall into the scope of the present application.

As shown in FIGS. 1 to 4, a hinge includes a V-shaped blade 1 or/and an intermediate blade 3 or/and a terminal blade 5. The V-shaped blade 1, the intermediate blade 3 and the terminal blade 5 are provided with holes to allow a fixing member of the scoliosis orthosis 6 to pass through; the V-shaped blade 1 is hinged to one end of the intermediate blade 3 for supporting the bending of a body; or/and another end of the intermediate blade 3 is hinged to the terminal blade 5 for supporting the bending of the body; or/and the V-shaped blade 1 is hinged to the terminal blade 5 for supporting the bending of the body; the number of the intermediate blade 3 is adjusted according to the actual required length.

An open end 13 of the V-shaped blade is of a "V" shape, which can be adjusted according to the structure of the body part. For example, if a contact portion of the open end 13 of the V-shaped blade is a neck, it can be set to a "V" shape; and if the contact portion is other arc portion of the body, it can be set to a "U" shape.

The holes provided on the V-shaped blade 1, the intermediate blade 3, and the terminal blade are: grooves, circular holes, triangular holes, and square holes.

The holes provided on the V-shaped blade 1, the intermediate blade 3, and the terminal blade 5 are: strip-shaped grooves 12 of the V-shaped blade are provided on both sides of the V-shaped blade 1; strip-shaped grooves 32 of the intermediate blade are provided on both sides of the intermediate blade 3; strip-shaped grooves 52 of the terminal blade are provided on both sides of the terminal blade 5, the rear end of the terminal blade 5 is a flat end 53 of the terminal blade.

The strip-shaped grooves 32 of the intermediate blade are provided in the middle of the intermediate blade 3; and the strip-shaped grooves 52 of the terminal blade are provided in the middle of the terminal blade 5.

The number of the strip-shaped grooves 12 of the V-shaped blade, the strip-shaped grooves 32 of the intermediate blade, and the strip-shaped grooves 52 of the terminal blade may be 1 to 20, and the number of the strip-shaped grooves is set according to the actual requirements.

The scoliosis orthosis is fixed to the body by a belt or other fixing member of the scoliosis orthosis 6 passing through the strip-shaped grooves 12 of the V-shaped blade, the strip-shaped grooves 32 of the intermediate blade, and the strip-shaped grooves 52 of the terminal blade. The number of the strip-shaped grooves 12 of the V-shaped blade is two for connecting a shoulder belt 7; the intermediate blade 3 has two furcated ends and several strip-shaped grooves which can be used to control the length of the hinge device, and the number or/and size of the intermediate blade 3 can be adjusted according to actual requirements and used to fix the orthosis.

One end of the V-shaped blade 1 is a furcated end 11 of the V-shaped blade; both ends of the intermediate blade 3 are furcated ends 31 of the intermediate blade; one end of the terminal blade 5 is a furcated end 51 of the terminal blade; the furcated end 11 of the V-shaped blade is hinged to the furcated end 31 of the intermediate blade at one end of the intermediate blade 3 by a first pin 2 of the orthopedic hinge assembly 2; and the furcated end 31 of the intermediate blade at another end of the intermediate blade 3 is hinged to the furcated end 51 of the terminal blade by a second pin 4 of the orthopedic hinge assembly.

Any two of the furcated end 11 of the V-shaped blade, the furcated ends 31 of the intermediate blade, and the furcated end 51 of the terminal blade may form a structure having at least one convex portion 111, 311, 511 and at least one concave portion 112, 312, and 512 are fitted to each other. The hinge method is not unique and includes other methods.

The shapes of the V-shaped blade 1, the intermediate blade 3, and the terminal blade 5 are adapted to a using part of the body.

The V-shaped blade 1, the intermediate blade 3, and the terminal blade 5 have a plate shape.

A garment with a corrective function is further provided according to the present application, which includes any one of the above orthopedic hinge assembly.

Figure 5:
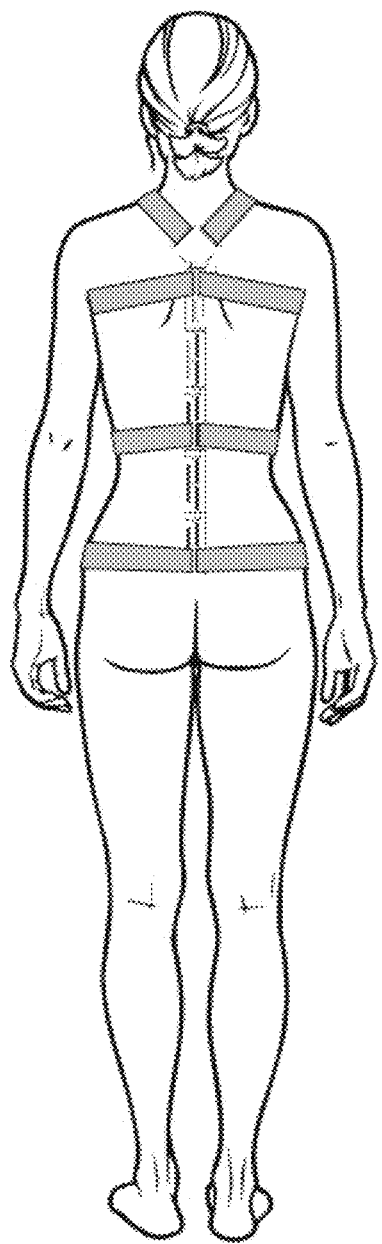
FIG. 5 is a schematic rear view of the orthopedic hinge assembly used in a spine according to the present application.
Figure 6:
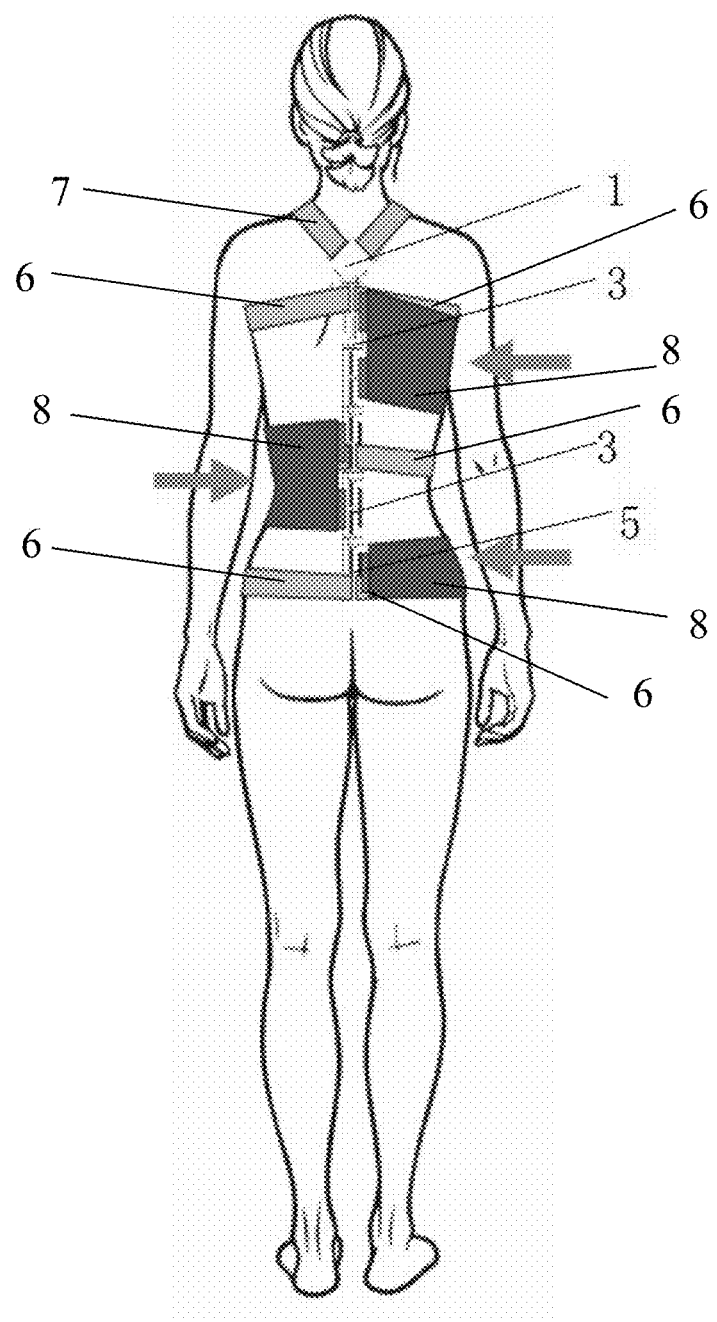
FIG. 6 is a schematic view showing the three-point pressure of a the orthopedic hinge assembly to a spine in a use state according to the present application.

In the embodiment, as shown in FIGS. 5 to 6, the adjustable external hinge according to the present application is used for a spinal orthosis, which includes the V-shaped blade 1 and three intermediate blades 3 and the terminal blade 5. The V-shaped blade 1, each intermediate blade 3, and the terminal blade 5 have a plate shape; the open end 13 of the V-shaped blade is a "V" shape and is adapted to a contact portion of a neck. The holes provided on the V-shaped blade 1, the intermediate blade 3, and the terminal blade 5 are: strip-shaped grooves 12 of the V-shaped blade that are provided on both sides of the V-shaped blade 1; strip-shaped grooves 32 of the intermediate blade that are provided on both sides of each intermediate blade 3; and strip-shaped grooves 52 of the terminal blade that are provided on both sides of the terminal blade 5.

The V-shaped blade 1 is hinged to one end of the intermediate blade 3 for supporting the bending of a body; another end of the intermediate blade 3 is hinged to the terminal blade 5 for supporting the bending of the body; the V-shaped blade 1 is hinged to the terminal blade 5 for supporting the bending of the body. The spinal orthosis is fixed to a back of the body by a belt passing through the strip-shaped grooves 12 of the V-shaped blade, the strip-shaped grooves 32 of the intermediate blade, and the strip-shaped grooves 52 of the terminal blade. The number of the strip-shaped grooves 12 of the V-shaped blade is two for connecting the shoulder belt 7; the corrective member 8 is stably fixed to one side of the body, thereby allowing the lateral corrective force to be effectively introduced; the hinge of each blade can support the forward bending of the body, thereby effectively introducing the corrective force, which is also consistent with the body movement; and the material used on each member can be rigid and can prevent the rotation of the orthosis and the loss of the corrective force. The system includes a main force acting in one direction and two reaction forces acting in opposite directions, which are located at proximal and distal ends of the main force. A corrective force is applied laterally to leave enough space on the other side of the body for effective body alignment and adaptive adjustment based on different parts of the body.

The above embodiments are only used to illustrate the technical solutions according to the present application, and are not limited thereto. Although the present application has been described in detail in conjunction with the foregoing embodiments, those of ordinary skill in the art will understand that: the technical solutions described in the foregoing embodiments may be modified, or some of the technical features may be equivalently replaced; and the modifications or replacements do not make the essence of the corresponding technical solutions deviate from the spirit and scope of the technical solutions of the various embodiments according to the present application.

The invention claimed is:

1. A hinge, which is configured to fix a scoliosis orthosis and vertically arranged at a back of a body along a spine of the body, wherein the hinge comprises:
   a V-shaped blade, and,
   an intermediate blade, and,
   a terminal blade,
   wherein the V-shaped blade, the intermediate blade, and the terminal blade have a plate shape and are connected with each other from top to bottom in sequence,
   wherein an open end of the V-shaped blade is "V" shaped and is adapted to fit a neck,
   wherein the V-shaped blade, the intermediate blade, and the terminal blade are each provided with holes to allow a fixing member of the scoliosis orthosis to pass through perpendicularly to thicknesses of the V-shaped blade, the intermediate blade, and the terminal blade, the V-shaped blade is hinged to an uppermost end of the intermediate blade for supporting a forward bending of the body; and a lowermost end of the intermediate blade is hinged to the terminal blade for supporting the forward bending of the body,
   wherein the holes of the V-shaped blade are configured to connect shoulder belts, and the holes of the intermediate blade and the terminal blade are configured to be connected with the scoliosis orthosis,
   wherein the scoliosis orthosis is configured to be fixed to the body by the shoulder belts by passing through the holes of the V-shaped blade, and the scoliosis orthosis is configured to be fixed to the body by the fixing member of the scoliosis orthosis or a corrective member of the scoliosis orthosis passing through the holes of the intermediate blade and the holes of the terminal blade thereby allowing a lateral corrective force to be introduced.

2. The hinge according to claim 1, wherein the holes provided on the V-shaped blade, the intermediate blade, and the terminal blade are: grooves, circular holes, triangular holes, or/and square holes.

3. The hinge according to claim 2, wherein the holes provided on the V-shaped blade, the intermediate blade, and the terminal blade are: 1 to 10 strip-shaped grooves of the V-shaped blade that are provided on both sides of the V-shaped blade; 1 to 20 strip-shaped grooves of the intermediate blade that are provided on both sides of the intermediate blade; 1 to 20 strip-shaped grooves of the terminal blade that are provided on both sides of the terminal blade.

4. The hinge according to claim 3, wherein 1 to 20 strip-shaped grooves of the intermediate blade are provided in the middle of the intermediate blade; and 1 to 20 strip-shaped grooves of the terminal blade are provided in the middle of the terminal blade.

5. The hinge according to claim 4, wherein one intermediate blade is provided, or 2 to 20 intermediate blades are provided.

6. The hinge according to claim 1, wherein one end of the V-shaped blade is a furcated end; both ends of the intermediate blade are furcated ends; one end of the terminal blade is a furcated end; the furcated end of the V-shaped blade is hinged to the furcated end at the uppermost end of the intermediate blade by a first hinge pin; and the furcated end at the lowermost end of the intermediate blade is hinged to the furcated end of the terminal blade by a second hinge pin.

7. The hinge according to claim 6, wherein any two of the furcated end of the V-shaped blade, the furcated ends of the intermediate blade, and the furcated end of the terminal blade form a structure having at least one convex portion and at least one concave portion are fitted to each other.

8. The hinge according to claim 7, wherein shapes of the V-shaped blade, the intermediate blade, and the terminal blade are coordinated with contour and motion of the body.

* * * * *